(12) United States Patent
Ridgley et al.

(10) Patent No.: US 10,231,816 B2
(45) Date of Patent: *Mar. 19, 2019

(54) MEDICAL DEVICES, SYSTEMS, AND KITS FOR THE MEDIALIZATION OF A VOCAL CORD

(71) Applicants: Cook Medical Technologies LLC, Bloomington, IN (US); Northwestern University, Evanston, IL (US)

(72) Inventors: Pamela Ridgley, Bloomington, IN (US); Darin Schaeffer, Bloomington, IN (US); Gordon Siegel, Chicago, IL (US); Marc Lim, Little Rock, AR (US)

(73) Assignees: Cook Medical Technologies LLC, Bloomington, IN (US); Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/481,681

(22) Filed: Apr. 7, 2017

(65) Prior Publication Data

US 2017/0209252 A1 Jul. 27, 2017

Related U.S. Application Data

(63) Continuation of application No. 14/840,098, filed on Aug. 31, 2015, now Pat. No. 9,615,918, which is a
(Continued)

(51) Int. Cl.
*A61F 2/20* (2006.01)
*A61B 17/24* (2006.01)
(Continued)

(52) U.S. Cl.
CPC ............. *A61F 2/02* (2013.01); *A61B 17/24* (2013.01); *A61B 17/3417* (2013.01);
(Continued)

(58) Field of Classification Search
CPC ........ A61F 2/20; A61B 17/24; A61B 17/3417
(Continued)

(56) References Cited

U.S. PATENT DOCUMENTS

D200,283 S 2/1965 Gershen
4,052,754 A 10/1977 Homsy
(Continued)

FOREIGN PATENT DOCUMENTS

EP 0453186 11/1991
EP 0856299 8/1998
(Continued)

OTHER PUBLICATIONS

Original French version of Written Opinion (PCT/ISA/237) for PCT/FR2008/000262 dated Sep. 1, 2008.
(Continued)

*Primary Examiner* — Suzette J Gherbi
(74) *Attorney, Agent, or Firm* — Buchanan Van Tuinen LLC

(57) ABSTRACT

Medical devices, systems, methods, and kits for the medialization of a vocal cord are described. A method comprises creating a passageway in thyroid cartilage of a patient, advancing a light source through the passageway, activating the light source, viewing light emitted from the light source to confirm placement of the passageway relative to the vocal cord, and advancing a medical device through the passageway to move the vocal cord toward a midline of the larynx of the patient.

20 Claims, 7 Drawing Sheets

Related U.S. Application Data continuation of application No. 13/974,451, filed on Aug. 23, 2013, now Pat. No. 9,119,712.

(60) Provisional application No. 61/693,139, filed on Aug. 24, 2012.

(51) Int. Cl.

| A61F 2/02 | (2006.01) |
|---|---|
| A61B 17/34 | (2006.01) |
| A61F 2/04 | (2013.01) |
| A61M 16/04 | (2006.01) |

(52) U.S. Cl.
CPC ............ *A61B 17/3468* (2013.01); *A61F 2/20* (2013.01); *A61F 2/203* (2013.01); *A61F 2002/046* (2013.01); *A61M 16/0465* (2013.01); *A61M 16/0472* (2013.01)

(58) Field of Classification Search
USPC ...................................................... 623/14.11
See application file for complete search history.

(56) References Cited

U.S. PATENT DOCUMENTS

| 4,094,303 A | 6/1978 | Johnston |
| 4,269,192 A | 5/1981 | Matsuo |
| 4,281,669 A | 8/1981 | Mac Gregor |
| 4,374,669 A | 2/1983 | Mac Gregor |
| 4,550,448 A | 11/1985 | Kenna |
| D284,507 S | 7/1986 | Leopoldi |
| 4,744,792 A | 5/1988 | Sander et al. |
| 4,745,910 A | 5/1988 | Day et al. |
| 4,863,476 A | 9/1989 | Shepperd |
| 4,938,234 A | 7/1990 | Capriotti |
| 5,197,482 A | 3/1993 | Rank et al. |
| 5,197,982 A | 3/1993 | Goldsmith, III et al. |
| 5,201,765 A | 4/1993 | Netterville et al. |
| 5,306,298 A | 4/1994 | Godley, III et al. |
| 5,326,375 A | 7/1994 | Montgomery et al. |
| 5,344,453 A | 9/1994 | Montgomery et al. |
| 5,358,522 A | 10/1994 | Montgomery et al. |
| 5,360,448 A | 11/1994 | Thramann |
| 5,376,076 A | 12/1994 | Kaali |
| 5,437,266 A | 8/1995 | McPherson et al. |
| 5,531,752 A | 7/1996 | Netterville et al. |
| 5,549,673 A | 8/1996 | Beale |
| 5,593,439 A | 1/1997 | Cummings et al. |
| 5,693,096 A | 12/1997 | Bettez et al. |
| 5,855,607 A | 1/1999 | Friedrich |
| 6,123,710 A | 9/2000 | Pinczewski et al. |
| 7,025,784 B1 | 4/2006 | Blom et al. |
| 9,084,675 B2 | 7/2015 | Eller et al. |
| 9,119,712 B2 | 9/2015 | Ridgley et al. |
| 9,615,918 B2* | 4/2017 | Ridgley ............. A61B 17/3417 |
| 2004/0254642 A1 | 12/2004 | Isshiki et al. |
| 2005/0154390 A1 | 7/2005 | Biedermann et al. |
| 2008/0023012 A1 | 1/2008 | Dineen et al. |
| 2008/0071230 A1 | 3/2008 | Lindenthaler |
| 2009/0044814 A1 | 2/2009 | Iancea et al. |
| 2010/0023125 A1 | 1/2010 | Debry et al. |
| 2011/0301580 A1 | 12/2011 | Hoffman |
| 2012/0055492 A1 | 3/2012 | Nikolchev et al. |
| 2012/0150293 A1 | 6/2012 | Hoffman et al. |
| 2012/0158137 A1 | 6/2012 | Pinczewski |
| 2013/0131733 A1 | 5/2013 | Chien et al. |
| 2013/0245639 A1* | 9/2013 | Lindenthaler ...... A61B 17/3468 606/129 |
| 2013/0303848 A1 | 11/2013 | Kahle et al. |
| 2014/0058509 A1 | 2/2014 | Ridgley et al. |
| 2014/0100612 A1 | 4/2014 | Suddaby |
| 2014/0163664 A1* | 6/2014 | Goldsmith ....... A61B 17/00491 623/1.11 |
| 2014/0195245 A1 | 7/2014 | Eller et al. |
| 2014/0288648 A1* | 9/2014 | Walder .................... A61F 2/203 623/9 |
| 2014/0336761 A1* | 11/2014 | Schaeffer .................. A61F 2/20 623/14.11 |
| 2014/0343359 A1* | 11/2014 | Farr ................... A61B 1/00052 600/109 |
| 2014/0378766 A1* | 12/2014 | Lo ..................... A61M 16/0495 600/120 |
| 2015/0164310 A1* | 6/2015 | Holt ..................... A61B 1/0646 600/199 |
| 2015/0242581 A1* | 8/2015 | Talbert ................ G06F 19/3406 348/65 |
| 2016/0008017 A1* | 1/2016 | Makower ............... A61B 5/411 600/424 |
| 2016/0015259 A1* | 1/2016 | Mody ...................... A61B 8/12 600/439 |
| 2016/0038014 A1* | 2/2016 | Molnar ............. A61M 16/0003 600/109 |

FOREIGN PATENT DOCUMENTS

| WO | 9006093 | 6/1990 |
| WO | 9221303 | 12/1992 |

OTHER PUBLICATIONS

English Translation of Written Opinion (PCT/ISA/237) for PCT/FR2008/000262 dated Sep. 1, 2008.
European Patent Office, Partial European Search Report, Patent App. No. 13181629, dated Nov. 22, 2013, pp. 1-5.
File history of U.S. Appl. No. 13/201,669 as of Aug. 11, 2014. Filing date, Aug. 16, 2011. First Named Inventor, Henry T. Hoffman. Title, Methods and devices for arytenoid repositioning.
Hoffman, Henry T., et al., "Arytenoid Repositioning Device," Annals of Otology, Rhinology & Laryngology, Mar. 2014, vol. 123, Issue 3, pp. 195-205.
Response to Office Action dated Sep. 6, 2013 for U.S. Appl. No. 13/201,669, submitted Jan. 7, 2014, pp. 1-5.
European Patent Office, Extended European Search Report, Patent App. No. EP13181629, dated Mar. 12, 2014. pp. 1-9.
Response to Office Action dated Apr. 28, 2014 for U.S. Appl. No. 13/201,669, submitted Oct. 28, 2014, pp. 1-9.
USPTO, Final Office Action dated Dec. 15, 2014 for U.S. Appl. No. 13/201,669, pp. 1-11.
USPTO, Non-final Office Action dated Apr. 28, 2014 for U.S. Appl. No. 13/201,669, pp. 1-9.
European Patent Office, European Examination Report, Patent App. No. EP13181629, dated Oct. 27, 2016. pp. 1-5.
European Patent Office, Extended European Search Report for application No. 17205721.8, dated Apr. 23, 2018, p. 1-7.

* cited by examiner

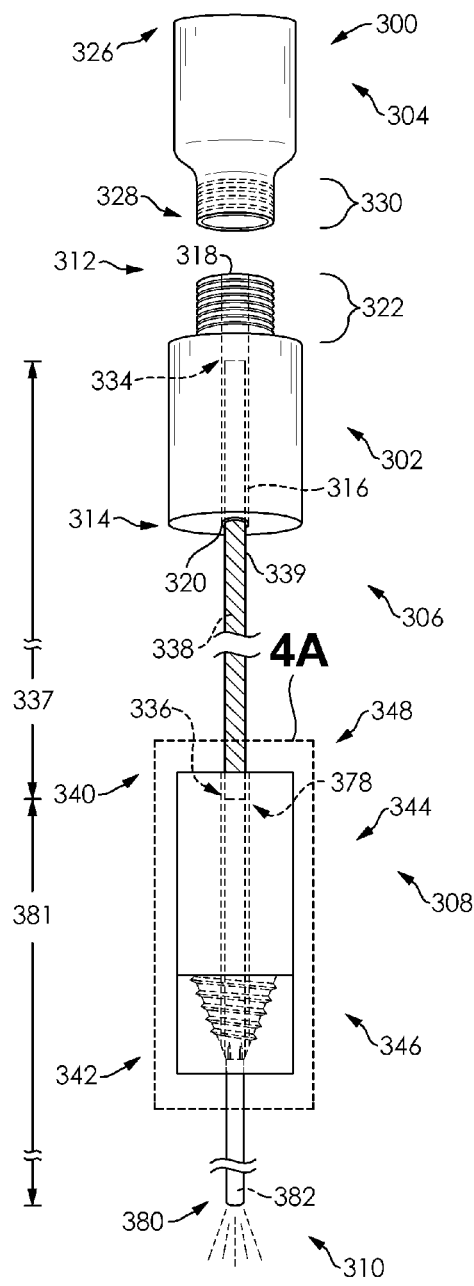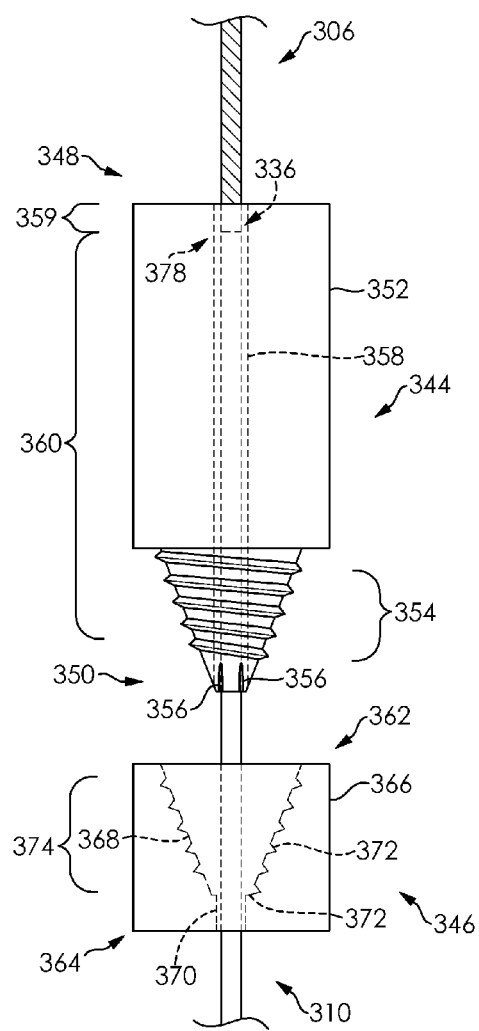
FIG. 4
FIG. 4A

MEDICAL DEVICES, SYSTEMS, AND KITS FOR THE MEDIALIZATION OF A VOCAL CORD

RELATED APPLICATIONS

This application is a continuation of U.S. Non-Provisional application Ser. No. 14/840,098, filed on Aug. 31, 2015, which is a continuation of U.S. Non-Provisional application Ser. No. 13/974,451, which was filed on Aug. 23, 2013, issued as U.S. Pat. No. 9,119,712 on Sep. 1, 2015, and which claims the benefit of U.S. Provisional Application No. 61/693,139, filed on Aug. 24, 2012. Each of these related applications is hereby incorporated into this disclosure in its entirety.

DESCRIPTION OF FIGURES

FIG. 4 illustrates an embodiment of a delivery system used to implant a medical device.

FIG. 4A is a magnified view of the elements in area 4A indicated in FIG. 4. In FIG. 4A a portion of the delivery system has been moved from a second configuration to a first configuration, as described in more detail below.

DESCRIPTION OF EMBODIMENTS

The following detailed description and the appended drawings describe and illustrate various example embodiments of medical devices, systems, methods, and kits for the medialization of a vocal cord. The description and illustration of these examples are provided to enable one skilled in the art to make and use a medical device, system, and kit and to practice a method of treatment using a medical device, system, and/or kit according to an embodiment. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The term "medication" refers to any fluid, drug, agent, therapeutic agent, and/or any other material used on a patient, or to treat a patient.

The use of "medialize" and grammatically related terms refers to the movement, and/or positioning, of an element or feature toward the midline of another element or feature (e.g., movement of a vocal cord toward the midline of the larynx).

Figure 1:
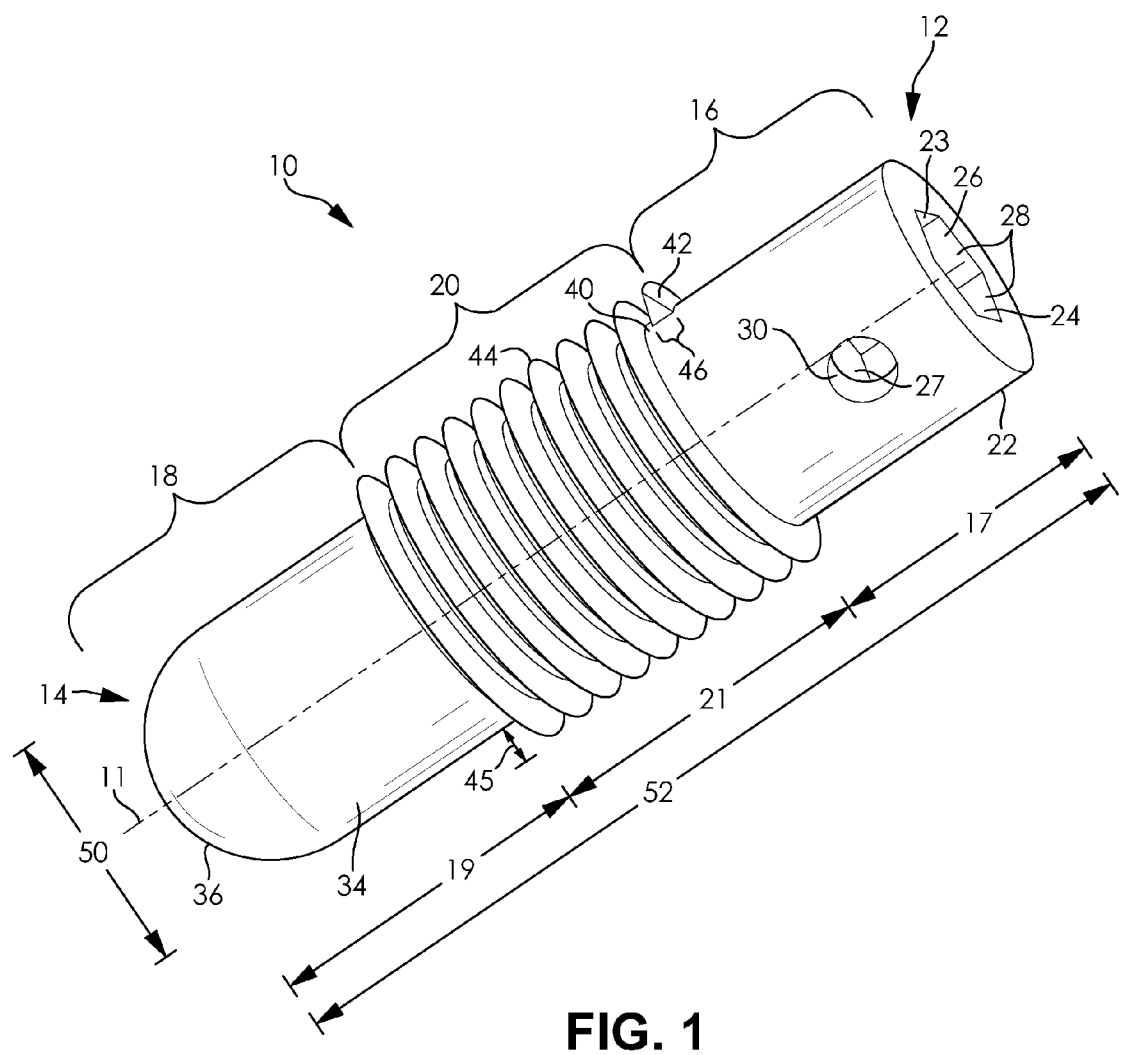
FIG. 1 illustrates a perspective view of an embodiment of a medical device.

FIG. 1 illustrates an embodiment of a medical device 10 that has a longitudinal axis 11, a proximal end 12, a distal end 14, a proximal portion 16, a distal portion 18, and an elongate body 20. Elongate body 20 is attached to the proximal portion 16 and the distal portion 18 and extends along the longitudinal axis 11 between the proximal portion 16 and the distal portion 18.

Attachment of the elongate body 20 to the proximal portion 16 and the distal portion 18 can be accomplished using any suitable method of attachment and skilled artisans will be able to select a suitable method of attachment according to a particular embodiment based on various considerations, including the materials forming each of the elements. Example methods of attachment considered suitable include, but are not limited to, using adhesives, mechanical connections, welds, and any other method of attachment considered suitable for a particular embodiment. Alternatively, the elongate body can be integrally formed with one or both of the proximal portion and the distal portion.

Figure 2:
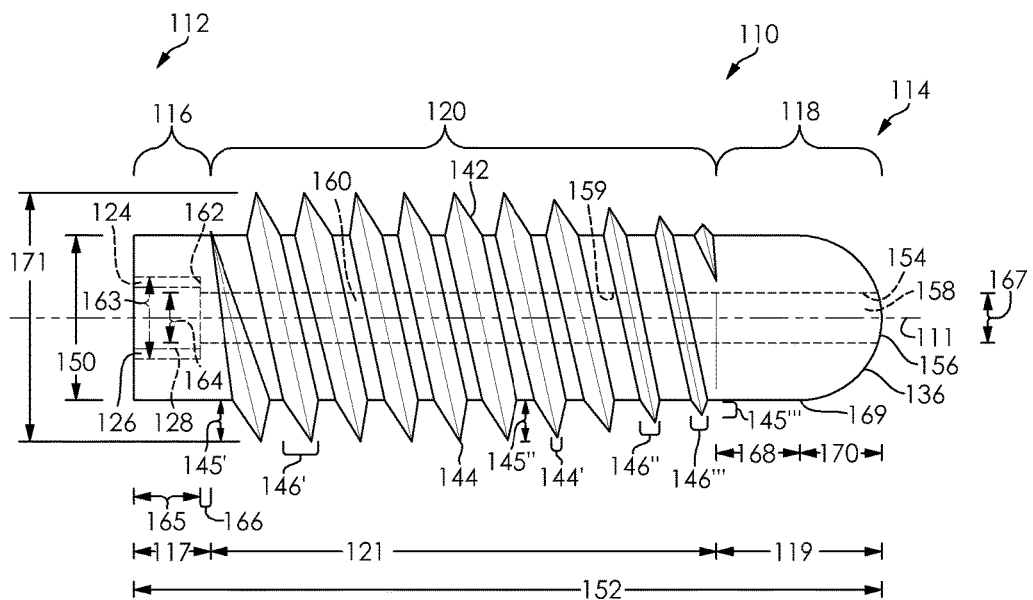
FIG. 2 illustrates a side view of another embodiment of a medical device.

Proximal portion 16 has an axial length 17, an outer surface 22, an inner surface 23, and defines a proximal opening 24, a proximal passageway 26, a series of facets 28, and an aperture 30. Axial length 17 extends along the longitudinal axis 11 of medical device 10 and from the proximal end 12 of medical device 10 to elongate body 20. Proximal opening 24 is defined on the proximal end 12 of medical device 10 and provides access to proximal passageway 26. Proximal passageway 26 is defined by inner surface 23 and extends through a portion of the axial length 17 of proximal portion 16 to a base 27. Alternatively, the proximal passageway of a medical device can extend through the entire axial length of the proximal portion, as shown in FIG. 2. The series of facets 28 are defined by inner surface 22, extend along a portion of the axial length 17 of proximal portion 16, and extend along the entire circumference of inner surface 22. Alternatively, the series of facets defined by the proximal portion of a medical device can extend along a portion of the circumference of the inner surface and/or along the entire axial length of the proximal portion. In the illustrated embodiment, the series of facets 28 define a hexagonal opening. Aperture 30 is disposed between the proximal end 12 of medical device 10 and elongate body 20 and extends through proximal portion 16 on an axis that passes through, and is orthogonal to, the longitudinal axis 11 of medical device 10. Alternatively, aperture 30 can be omitted from medical device 10, or an aperture can be disposed on an axis that does not pass through the longitudinal axis of a medical device.

Figure 5:
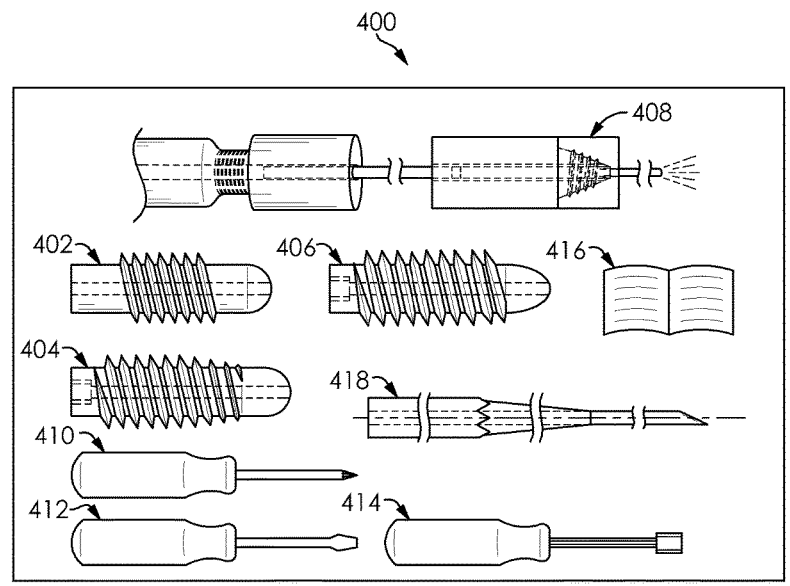
FIG. 5 illustrates an embodiment of a kit.

Proximal passageway 26 and the series of facets 28 defined by proximal portion 16 are sized and configured to receive a portion of a delivery tool, shown in FIG. 5, that has a distal end complementary to the proximal passageway 26 and the series of facets 28. The delivery tool is sized and configured to engage the inner surface 22 and the series of facets 28 to deliver medical device 10 at a point of treatment (e.g., by applying torque to the delivery tool that is transferred to medical device 10). Optionally, a delivery tool can define a passageway that extends from a first opening defined on the proximal end of the delivery tool to a second opening defined on the distal end of the delivery tool. The passageway defined by the delivery tool can be used to guide the delivery tool over a wire guide, or light fiber, toward a point of treatment, as described in more detail below. While the illustrated series of facets 28 define a hexagonal opening, the series of facets of a medical device can define any suitable opening sized and configured to receive a portion, or the entirety, of a delivery tool, and skilled artisans will be able to select a suitable opening for a series of facets to define according to a particular embodiment based on various considerations, including the type of delivery tool intended to be used with the medical device. Example openings considered suitable for a series of facets to define include, but are not limited to, hexagonal, triangular, square, pentagonal, slotted, cross-recesses, Phillips, Frearson, French recess, Mortorq, Pozidriv, Supadriv, Robertson, hex socket, hexalobular, TTAP, Phillips-square, Bristol, spline, spanner, Torq-set, TP3, tri-wing, triple square, or any other opening considered suitable for a particular application.

Aperture 30 is sized and configured to receive a portion of a delivery tool (not illustrated) such that the portion of the delivery tool can engage the surface of the proximal portion 16 defining the aperture 30 to deliver medical device 10 at a point of treatment. While the illustrated aperture 30 defines a circular opening, the aperture of a medical device can define any suitable opening sized and configured to receive a portion, or the entirety, of a delivery tool, and skilled artisans will be able to select a suitable opening for an aperture to define according to a particular embodiment based on various considerations, including the type of delivery tool intended to be used with the medical device. Example openings considered suitable for an aperture to define include, but are not limited to, those described above.

Distal portion 18 has an axial length 19 and an outer surface 34. Axial length 19 extends along the longitudinal axis 11 of medical device 10 and from elongate body 20 to the distal end 14 of medical device 10. Outer surface 34 defines a curved surface to provide an atraumatic distal tip 36. While the outer surface 34 has been illustrated as curved, the outer surface of the distal portion of a medical device can have any suitable configuration, including, but not limited to, flat, substantially flat, hemispherical, rounded, convex, substantially convex, parabolic, domed, half-polyhedron, and any other configuration considered suitable for a particular embodiment. Alternatively, the distal portion of a medical device can define a distal passageway that extends through the axial length of the distal portion, such as distal passageway 158 illustrated in FIG. 2.

Elongate body 20 has an axial length 21, an outer surface 40, and defines a thread 42. Axial length 21 extends along the longitudinal axis 11 of medical device 10 and from the proximal portion 16 to the distal portion 18. In the illustrated embodiment, outer surface 40 is cylindrical in shape. The outer surface 40 can have any configuration, though, such as polygonal, or any other configuration considered suitable for a particular application. Thread 42 has a free edge 44, a depth 45, and a thickness 46 and extends from proximal portion 16 to distal portion 18. Thread 42 extends outward from outer surface 40 relative to the longitudinal axis 11 to free edge 44. Thread 42 extends along the outer surface 40 and along longitudinal axis 11 through a plane that contains the midpoint of medical device 10 and extends orthogonally through longitudinal axis 11. The depth 45 of thread 42 extends from outer surface 40 to free edge 44 and is measured on an axis that is normal to the longitudinal axis 11. In the illustrated embodiment, thread 42 has a constant depth 45. However, alternative embodiments can include a thread that has a varying depth. Thickness 46 is measured on a plane that extends parallel to longitudinal axis 11. In the illustrated embodiment, thread 42 has a constant thickness 46. However, alternative embodiment can include a thread that has a varying thickness. In use, thread 42 is sized and configured to engage a wall that defines a passageway in a body (e.g., thyroid cartilage that defines a passageway created adjacent to a vocal cord). Alternatively, the elongate body of a medical device can define a main passageway that extends through the axial length of the medical device, such as main passageway 160 illustrated in FIG. 2.

While the illustrated thread 42 extends from the proximal portion 16 to the distal portion 18, the thread of a medical device can extend along any suitable length of the medical device. Skilled artisans will be able to select a suitable length for a thread of a medical device according to a particular embodiment based on various considerations, including the configuration of the passageway defined at a point of treatment that the medical device is intended to be used. Example lengths considered suitable for a thread of a medical device include, but are not limited to, a thread that extends along the entire axial length of the proximal portion, distal portion, and elongate body, a thread that extends along a portion of the axial length of the elongate body, a thread that extends between the proximal portion and the distal portion, a thread that extends along a portion of the axial length of the distal portion and along the entire axial length of the elongate body and the proximal portion, a thread that extends along the entire axial length of the elongate body and the proximal portion, a thread that extends along a portion of the axial length of the elongate body and the entire axial length of the proximal portion, a thread that extends along a portion of the axial length of the elongate body and a portion of the axial length of the proximal portion, a thread that extends along the entire axial length of the elongate body and a portion of the axial length of the distal portion, a thread that extends along a portion of the axial length of the proximal portion and the distal portion and the entire axial length of the elongate body, and any other length considered suitable for a particular application.

In the illustrated embodiment, medical device 10 is formed of a first material. Any suitable material can be used to form a medical device, and skilled artisans will be able to select a suitable material according to a particular embodiment based on various considerations, including the material(s) at a point of treatment that the medical device is intended to be used. Example materials considered suitable to form a medical device include, but are not limited to, biocompatible materials, materials that can be made biocompatible, metals, tantalum, titanium, inconel, metal alloy, low-carbon stainless steel, cobalt-chromium-molybdenum, cobalt-nickel-chromium-molybdenum, titanium alloy, $Ti_6Al_4V$, plastics, polyethylene, polyethylene terephthalate, poly-L-lactide, polytetrafluoroethylene (PTFE), and any other material considered suitable for a particular application.

Alternatively, the proximal portion of a medical device can be formed of a first material, the distal portion of the medical device can be formed of a second material, and the elongate body of the medical device can be formed of a third material. The first material can be the same as, or different from, the second material and/or the third material, the second material can be the same as, or different from, the first material and/or the third material, and the third material can be the same as, or different from, the first material and/or second material. Example materials considered suitable to form the proximal portion, distal portion, and/or elongate body of a medical device include, but are not limited to, those described above. For example, the distal portion can be formed of a first material (e.g., plastic) and the proximal portion and/or the elongate body can be formed of a second material (e.g., metal). The first material can have the same, or different, characteristics as the second material. For example, the first material can be flexible, or soft, relative to the second material, or the second material can be rigid relative to the first material.

In the illustrated embodiment, medical device 10 has an outside diameter 50 along the proximal portion 12, distal portion 14, and elongate body 16, which does not include the depth 45 of thread 42. The inventors have determined that medical devices having an outside diameter of at least 1 millimeter, but less than or equal to 10 millimeters are considered suitable. The inventors have also determined that medical devices having an outside diameter of at least 2 millimeters, but less than or equal to 9 millimeters are considered suitable. The inventors have also determined that medical devices having an outside diameter of at least 3 millimeters, but less than or equal to 8 millimeters are considered suitable. The inventors have also determined that medical devices having an outside diameter of at least 4 millimeters, but less than or equal to 7 millimeters are considered suitable.

In the illustrated embodiment, medical device 10 has a length 52 that extends along the longitudinal axis 11 and is equal to the sum of the axial length 17 of proximal portion 16, the axial length 19 of distal portion 18, and the axial length 21 of elongate body 20. The inventors have determined that medical devices having a length of at least 5 millimeters, but less than or equal to 17 millimeters are considered suitable. The inventors have also determined that medical devices having a length of at least 6 millimeters, but less than or equal to 16 millimeters are considered suitable. The inventors have also determined that medical devices having a length of at least 7 millimeters, but less than or equal to 15 millimeters are considered suitable. The inventors have also determined that medical devices having a length of at least 8 millimeters, but less than or equal to 14 millimeters are considered suitable. The inventors have also determined that medical devices having a length of at least 9 millimeters, but less than or equal to 13 millimeters are considered suitable. The inventors have also determined that medical devices having a length of at least 10 millimeters, but less than or equal to 12 millimeters are considered suitable.

FIG. 2 illustrates another medical device 110. Medical device 110 is similar to medical device 10 illustrated in FIG. 1 and described above, except as detailed below. Reference numbers in FIG. 2 refer to the same structural element or feature referenced by the same number in FIG. 1, offset by 100. Thus, medical device 110 comprises a longitudinal axis 111, a proximal end 112, a distal end 114, a proximal portion 116, a distal portion 118, and an elongate body 120.

In the illustrated embodiment, medical device 110 omits the inclusion of an aperture defined on proximal portion 116 (e.g., aperture 30 illustrated in FIG. 1), distal portion 118 has an inner surface 154 and defines a distal opening 156 and a distal passageway 158, elongate body 120 has an inner surface 159 and defines a main passageway 160, and the depth 145 of thread 142 decreases from the proximal end of the thread 142 to the distal end of the thread 142. In addition, distal portion 118 is formed of a first material and elongate body 120 is formed of a second material that is different than the first material. The second material is rigid relative to the first material. For example, the first material can be a plastic, or other non-metallic material, and the second material can be a metal, or other material that is rigid relative to the first material. Additional features of medical device 110 will be described in more detail below. While medical device 110 has been described as omitting the inclusion of an aperture defined on the proximal portion 116 (e.g., aperture 30 illustrated in FIG. 1), an alternative embodiment can include an aperture defined on the proximal portion of a medical device.

Proximal portion 116 defines a shoulder 162 within proximal passageway 126 such that proximal passageway 126 has a first inside diameter 163 and a second inside diameter 164. The first inside diameter 163 is greater than the second inside diameter 164 and extends along a first portion 165 of the axial length 117 of proximal portion 116. The second inside diameter 164 extends along a second a portion 166 of the axial length 117 of proximal portion 116 that extends from the distal end of the first portion 165 to elongate body 120. Alternatively, proximal portion 116 can omit the inclusion of a shoulder 162 and define a passageway that has a continuous, or substantially continuous, inside diameter that is equal to, or substantially equal to, the inside diameter of the main passageway 160 defined by elongate body 120.

In the illustrated embodiment, each of the proximal opening 124 and the series of facets 128 have an inside diameter that is equal to the first inside diameter 163, which is sized and configured to receive a portion of a delivery tool (e.g., shown in FIG. 5). In the illustrated embodiment, the first inside diameter 163 is 1.0 millimeter. However, the first inside diameter can have any suitable length. Skilled artisans will be able to select a suitable length for the first inside diameter of a proximal portion according to a particular embodiment based on various considerations, including the outside diameter of the delivery tool being passed through the proximal opening of the proximal portion. Example inside diameters considered suitable for the first inside diameter of a medical device include, but are not limited to, an inside diameter between 0.8 millimeters and 1.2 millimeters, an inside diameter between about 0.8 millimeters and about 1.2 millimeters, an inside diameter equal to 1.0 millimeter, an inside diameter equal to about 1.0 millimeter, and any other inside diameter considered suitable for a particular embodiment.

In the illustrated embodiment, the first portion 165 of the axial length 117 of proximal portion 116 has a length that is 0.8 millimeters and the second portion 166 of the axial length 117 of proximal portion 116 has a length that is 0.2 millimeters. Thus, the axial length 117 of proximal portion 116 is 1.0 millimeter. However, the first portion 165 of the axial length 117, the second portion 166 of the axial length 117, and the axial length 117 of proximal portion 116 can have any suitable length. Skilled artisans will be able to select a suitable length for each of the first portion of the axial length of a proximal portion, the second portion of the axial length of a proximal portion, and/or the axial length of a proximal portion according to a particular embodiment based on various considerations, including the depth of a passageway defined at a point of treatment. Examples of lengths considered suitable include, but are not limited to, a first portion that has a length between 0.6 millimeters and 1.2 millimeters, a first portion that has a length between about 0.6 millimeters and about 1.2 millimeters, a second portion that has a length between 0.1 millimeters and 0.4 millimeters, a second portion that has a length between about 0.1 millimeters and about 0.4 millimeters, a proximal portion that has an axial length between 0.6 millimeters and 1.4 millimeters, a proximal portion that has an axial length between about 0.6 millimeters and about 1.4 millimeters, a proximal portion that has an axial length equal to 1.0 millimeter, a proximal portion that has an axial length equal to about 1.0 millimeter, and any other length considered suitable for a particular embodiment.

Distal opening 156 is defined on the distal end 114 of medical device 110 and provides access to distal passageway 158 that extends through the entire axial length 119 of distal portion 118 and along the longitudinal axis 111. Main passageway 160 defined by elongate body 120 extends through the entire axial length 121 of elongate body 120 and is in communication with each of the proximal passageway 126 and the distal passageway 158. Thus, medical device 110 has a passageway extending through its entire length 152. While not illustrated, and alternative embodiment of a medical device can omit the inclusion of a proximal passageway, main passageway, and/or distal passageway.

In the illustrated embodiment, each of the distal passageway 158 and main passageway 160 has an inside diameter 167. The second inside diameter 164 of proximal passageway 126 and inside diameter 167 are each sized and configured to receive a wire guide, lit wire guide, light fiber, or any other device considered suitable to pass through medical device 110. In the embodiment illustrated in FIG. 2, the second inside diameter 164 and inside diameter 167 are the same and equal to 0.6 millimeters. However, the inside diameter of a proximal passageway, distal passageway, and/or main passageway can have any suitable length, and skilled artisans will be able to select a suitable length for the inside diameter of a proximal passageway, distal passageway, and/or main passageway of a medical device according to a particular embodiment based on various considerations, including the outside diameter of a device being passed through a passageway. Example lengths considered suitable for the inside diameter of the proximal passageway, distal passageway, and/or main passageway of a medical device include, but are not limited to, a length between 0.4 millimeters and 0.8 millimeters, a length between about 0.4 millimeters and about 0.8 millimeters, a length equal to 0.6 millimeters, a length equal to about 0.6 millimeters, and any other length considered suitable for a particular embodiment.

In the illustrated embodiment, a first portion 168 of the axial length 119 of distal portion 118 extends from elongate body 120 to a location 169 between the elongate body 120 and the distal end 114 of medical device 110. A second portion 170 of the axial length 119 of distal portion 118 extends from location 169 to the distal end 114 of medical device 110. The curve of distal portion 118 that defines atraumatic distal tip 136 extends along the second portion 170 of axial length 119. Alternatively, the curve of a distal portion of a medical device can extend from the elongate body to the distal end of the medical device, as shown in the embodiment illustrated in FIG. 3.

In the illustrated embodiment, the length of first portion 168 of the axial length 119 of distal portion 118 is 1.0 millimeter and the length of second portion 170 of the axial length 119 of distal portion 118 is 1.0 millimeter. However, other lengths are considered suitable for the first portion and second portion of the axial length of a distal portion. Skilled artisans will be able to select a suitable length for the first portion and/or second portion of the axial length of a distal portion according to a particular embodiment based on various considerations, including the structural configuration of a passageway defined at a point of treatment. Example lengths considered suitable for the first portion and/or second portion of the axial length of a distal portion include, but are not limited to, a length equal to 1.0 millimeter, a length equal to about 1.0 millimeter, a length between 0.8 millimeters and 1.2 millimeters, a length between about 0.8 millimeters and about 1.2 millimeters, and any other length considered suitable for a particular application.

In the illustrated embodiment, the length of the axial length 121 of elongate body 120 is equal to 5.0 millimeters. However, other lengths are considered suitable for elongate body 120, and skilled artisans will be able to select a suitable length for the axial length of the elongate body of a medical device according to a particular embodiment based on various considerations, including the structural configuration at a point of treatment. Example axial lengths considered suitable for an elongate body include, but are not limited to, an axial length between 4.0 millimeters and 6.0 millimeters, an axial length between about 4.0 millimeters and about 6.0 millimeters, an axial length equal to 5.0 millimeters, an axial length equal to about 5.0 millimeters, and any other length considered suitable for a particular embodiment.

The depth 145 of thread 142 extends from outer surface 140 to free edge 144 and is measured on an axis that is normal to the longitudinal axis 111. In the embodiment illustrated in FIG. 2, thread 142 has a first depth 145', a second depth 145", and a third depth 145'" (e.g., is self-tapping). The first depth 145' is disposed proximal to the second depth 145", the second depth 145" is disposed between the first depth 145' and the third depth 145'", and the third depth 145'" is disposed distal to the first depth 145' and the second depth 145". The first depth 145' is greater than the second depth 145" and the second depth 145" is greater than the third depth 145'". The first depth 145' is 0.5 millimeters and the third depth is 0.0 millimeters. Thus, thread 142 has a depth that varies along the length 152 of medical device 110. This structural arrangement provides a major diameter 171 of 3.0 millimeters for thread 142. Alternatively, a thread can have a first depth that is equal to, or equal to about, 0.75 millimeters and/or a third depth that is equal to, or equal to about, 0.0 millimeters. While thread 142 has been illustrated as having a particular depth 145 at various locations along the axial length 121 of elongate body 120, a thread can have any suitable depth along the axial length of an elongate body. Skilled artisans will be able to select a suitable depth for a thread according to a particular embodiment based on various considerations, including the diameter of a passageway defined at a point of treatment. Example depths (e.g., first depth, second depth, third depth) considered suitable for a thread include, but are not limited to, a depth between 0.25 millimeters and 0.75 millimeters, a depth between about 0.25 millimeters and about 0.75 millimeters, a depth equal to 0.5 millimeters, a depth equal to about 0.5 millimeters, and any other depth considered suitable for a particular embodiment.

Thread 142 has a first thickness 146', a second thickness 146", and a third thickness 146'" at outer surface 140 of elongate body 120. Each of the first thickness 146', second thickness 146", and third thickness 146'" is measured on a plane that extends parallel to longitudinal axis 111. Alternatively, the first thickness can be measured on a first plane, the second thickness can be measured on a second plane, and the third thickness can be measured on a third plane. In this alternative embodiment, each of the first, second, and third plane are parallel to the longitudinal axis of a medical device but are different from each other. The first thickness 146' is disposed proximal to the second thickness 146", the second thickness 146" is disposed between the first thickness 146' and the third thickness 146''' and is less than the first thickness 146', and the third thickness 146''' is disposed distal to the second thickness 146" and is less than the second thickness 146". Free edge 144 of thread 142 has a thickness 144'. The first thickness 146' at outer surface 140 is greater than the thickness 144' at free edge 144, the second thickness 146" at outer surface 140 is greater than the thickness 144' at free edge 144, and the third thickness 146''' at outer surface 140 is greater than the thickness 144' at free edge 144. Thus, thread 142 has a thickness 146 that varies along the length 152 of medical device 110. In addition, thread 142 tapers from the outer surface 140 of elongate body 120 to free edge 144 along depth 145.

Thread 142 can have any suitable pitch and skilled artisans will be able to select a suitable pitch for the thread of a medical device according to a particular embodiment based on various considerations, including the desired accuracy of the placement of the medical device at a point of treatment (e.g., within passageway defined by thyroid cartilage). The pitch of thread 142 is the distance from a first crest of thread 142 to an adjacent second crest of thread 142. Each of the first crest and second crest is disposed on an axis that is parallel to the longitudinal axis 111. Example pitches considered suitable for a thread include pitches equal to 0.6 millimeters, pitches equal to about 0.6 millimeters, pitches that vary along the length of a medical device, and any other pitch considered suitable for a particular embodiment.

In the illustrated embodiment, the outer surface 140 of elongate body 120 disposed between each turn of thread 142 (e.g., root of thread) is parallel to the longitudinal axis 111 of medical device 110 and increases in length from the proximal end of elongate body 120 to the distal end of elongate body 120. Thus, the outer surface 140 of elongate body 120 has a first length, a second length, and a third length. The first length is disposed proximal to the second length, the second length is disposed between the first and third lengths, and the third length is disposed distal to the second length. The first length is greater than the second length and the second length is greater than the third length. Alternatively, the outer surface 140 of the elongate body 120 of a medical device can be disposed at an angle to the longitudinal axis of the medical device and/or the outer surface of the elongate body of a medical device can have a constant length between each turn of the thread of the medical device.

In the illustrated embodiment, medical device 110 has an outside diameter 150 and a length 152. Outside diameter 150 has a length equal to 2.0 millimeters and length 152 is equal to 9.0 millimeters. However, other outside diameters and lengths are considered suitable for a medical device, and skilled artisans will be able to select a suitable outside diameter and length for a medical device according to a particular embodiment based on various considerations, including the diameter and depth of a passageway defined at a point of treatment. Example outside diameters considered suitable for a medical device include, but are not limited to, an outside diameter equal to 2.0 millimeters, an outside diameter equal to about 2.0 millimeters, outside diameters that taper along the length of a medical device, outside diameters that taper along a portion of the length of a medical device (e.g., proximal portion, distal portion, elongate body), outside diameters that taper from the proximal end to the distal end of the medical device, those described above with respect to medical device 10 illustrated in FIG. 1, and any other outside diameter considered suitable for a particular embodiment. Example lengths considered suitable for a medical device include, but are not limited to, a length equal to 9.0 millimeters, a length equal to about 9.0 millimeters, those described above with respect to medical device 10 illustrated in FIG. 1, and any other length considered suitable for a particular application.

In an alternative embodiment, a medical device can have an outer surface that has a first portion, a second portion, and a third portion. The first portion extends from the proximal end of the medical device toward the distal end and to the second portion. The second portion is disposed between the first portion and third portion. The third portion extends from the distal end of the medical device toward the proximal end and to the second portion. The first portion has a first outside diameter, the second portion has an outside diameter that tapers toward the distal end of the medical device, and the third portion has a third outside diameter. Thus, the second portion is tapered. The first outside diameter is greater than the third outside diameter and the second outside diameter tapers from the first outside diameter to the third outside diameter. The tapered second portion can be disposed on any suitable portion of a medical device, such as the proximal portion, distal portion, and/or elongate body. For example, the tapered second portion can be disposed on the elongate body and extend from the distal end of the elongate body toward the proximal end of the medical device. The proximal end of the second portion can be disposed between the proximal portion and the distal portion or at the proximal end of the elongate body. Alternatively, the second portion can be disposed on both the proximal portion and the elongate body or the elongate body and the distal portion.

Figure 3:
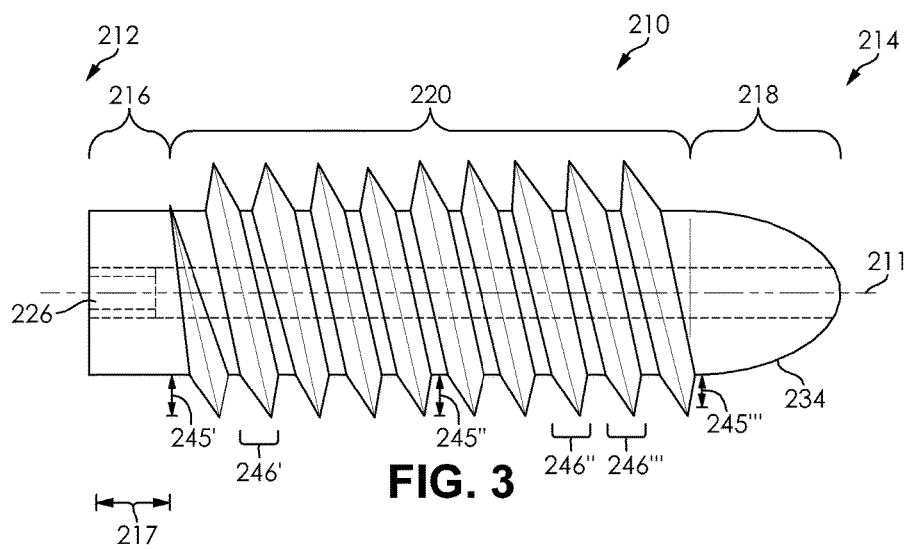
FIG. 3 illustrates a side view of another embodiment of a medical device.

FIG. 3 illustrates another medical device 210. Medical device 210 is similar to medical device 110 illustrated in FIG. 2 and described above, except as detailed below. Reference numbers in FIG. 3 refer to the same structural element or feature referenced by the same number in FIG. 2, offset by 100. Thus, medical device 210 comprises a longitudinal axis 211, a proximal end 212, a distal end 214, a proximal portion 216, a distal portion 218, and an elongate body 220. An alternative embodiment can include an aperture defined on the proximal portion of a medical device (e.g., aperture 30 illustrated in FIG. 1).

In the embodiment illustrated in FIG. 3, the proximal portion 216 omits the inclusion of a shoulder (e.g., shoulder 162 illustrated in FIG. 2) and defines a proximal passageway 226 that has a constant inside diameter along the axial length 217 of proximal portion 216. In addition, the outer surface 234 of distal portion 218 defines the curved surface from the elongate body 220 to the distal end 214 of the medical device 210. The first thickness 246' of thread 242 at outer surface 240 is the same as the second thickness 246" at outer surface 240 and the third thickness 246''' at outer surface 240 and the first depth 245' of thread 242 is the same as the second depth 245" and the third depth 245'''. Thus, thread 242 has a constant depth 245 and thickness 246 along the length of medical device 210 and the outer surface 240 of elongate body 220 has a constant length between each turn of thread 242.

FIGS. 4 and 4A illustrate an embodiment of a delivery system 300 used to implant, or assist with implanting, any suitable medical device according to an embodiment, such as the embodiments described and illustrated herein. Skilled artisans will be able to select a suitable medical device to use with system 300 according to a particular embodiment based on various considerations, including the treatment intended to be performed. Example medical devices considered suitable to use with system 300 include, but are not limited to, medical device 10, medical device 110, medical device 210, and any other medical device considered suitable for a particular application.

System 300 comprises a housing 302, a light source 304, a first light fiber 306, a handle 308, and a second light fiber 310. Optionally, a system could include a medical device, such as those described herein, disposed on the second light fiber 310.

Housing 302 has a proximal end 312, a distal end 314, and defines a passageway 316 extending from a first opening 318 defined at the proximal end 312 to a second opening 320 defined at the distal end 314. Each of the passageway 316, first opening 318, and second opening 320 is sized and configured to receive a portion of first light fiber 306. The proximal end 312 of housing 302 has a threaded portion 322 that is complementary to threaded portion 330 of light source 304, described below, such that housing 302 can be attached to light source 304. Alternatively, a light source can be an integrated component of a housing. While a threaded attachment has been illustrated between housing 302 and light source 304, any suitable method of attachment can be used, such as snap fit configurations, and any other method of attachment considered suitable for a particular application.

Light source 304 has a proximal end 326 and a distal end 328. Distal end 328 has a threaded portion 330 that is complementary to threaded portion 322 of housing 302 such that light source 304 can be attached to housing 302. Light source 304 can comprise any suitable light source, and skilled artisans will be able to select a suitable light source to include in a delivery system according to a particular embodiment based on various considerations, including the bodily passage within which the delivery system is intended to be used. Example light sources considered suitable include, but are not limited to, commercially-available light sources such as xenon, laser, LED, halogen light sources, and any other light source considered suitable for a particular embodiment. Optionally, light source 304 can include a fiber coupling (not shown) which provides communication between the light source and first light fiber 306. Alternative embodiments include incorporating a light source within a housing, integrally forming the housing and light source, or omitting the inclusion of a housing such that a first light fiber is operably attached directly to the light source.

First light fiber 306 is operably attached to the light source 304 and has a proximal end 334, a distal end 336, a length 337 extending from the proximal end 334 to the distal end 336, and defines a light path 338 extending along its length 337. In the illustrated embodiment, first light fiber 306 has an outside diameter equal to 0.5 millimeters. First light fiber 306 is disposed through second opening 320 defined by housing 302 such that the proximal end 334 of first light fiber 306 is disposed within housing 302. Alternatively, the proximal end of a first light fiber can be disposed proximal to the proximal end of a housing. First light fiber 306 is attached to housing at one or more locations along its length using any suitable method of attachment, such as adhesives, those described herein, and any other method of attachment considered suitable for a particular application. For example, first light fiber 306 can be attached to housing 302 at second opening 320, within passageway 316 of housing 302, at first opening 318, at proximal end 334, and/or any other location considered suitable for a particular embodiment. Proximal end 334 is disposed within housing 302 such that light generated by light source 304 can travel through the light path 338 defined by first light fiber 306.

First light fiber 306 has a coating 339 disposed along the entire circumference of the outer surface of first light fiber 306 and extends along its entire length 337. Alternatively, a coating can extend along a portion of the circumference of the outer surface of a first light fiber and/or along a portion of the length of a light fiber. First light fiber 306 comprises a first material and coating 339 comprises a second material that is different than the first material. Second material can comprise any suitable material, such as a plastic, those described herein, and any other material considered suitable for a particular embodiment. Optionally, coating 339 can be omitted from first light fiber 306. In the illustrated embodiment, first light fiber 306 has a length equal to 2.0 feet and an outside diameter equal to 0.5 millimeters.

Handle 308 comprises a proximal end 340, a distal end 342, a first portion 344, and a second portion 346. The handle 308 has a first configuration and a second configuration, each described in more detail below. FIG. 4 shows handle 308 in the second configuration and FIG. 4A shown handle 308 in the first configuration. While handle 308 has been illustrated as having a particular structural configuration, a handle can have any suitable structural configuration that is capable of releasably attaching a light fiber to the handle.

First portion 344 comprises a proximal end 348, a distal end 350, a shaft 352, a threaded portion 354, and projections 356. Shaft 352 extends from the proximal end 348 toward the distal end 350. Threaded portion 354 extends from distal end of the shaft 352 toward the distal end 350 of first portion 344. Projections 356 extend from the distal end of the threaded portion 354 to the distal end 350 of first portion 344 and form a collet configuration. Each of the projections 356 can optionally include one or more teeth and or ridges on a portion, or the entirety, of the interior surface of the projection to assist with attachment of a light fiber to handle 308. The body of shaft 352 and threaded portion 354 define passageway 358 that extends from the proximal end 348 of first portion 344 to the distal end of the threaded portion 354. A proximal portion 359 of passageway 358 is sized and configured to receive a portion of first light fiber 306 and a distal portion 360 is sized and configured to receive a portion of second light fiber 310. In the illustrated embodiment, each of the proximal portion 359 and distal portion 360 has the same inside diameter. Alternatively, the first portion and second portion of a passageway can have different inside diameters.

Second portion 346 comprises a proximal end 362, a distal end 364, and a shaft 366 that defines a recess 368 and a passageway 370. Shaft 366 extends from the proximal end 362 to the distal end 364. Recess 368 extends into shaft 366 from the proximal end 362 toward the distal end 364 to a recess base 372. The wall of recess 368 defines threaded portion 374 that extends from the proximal end 362 toward the distal end 364. Recess 368 tapers from the proximal end 362 to recess base 372 and is sized and configured to receive the threaded portion 354 and projections 356 of the first portion 344. Passageway 370 extends from a first opening on recess base 372 to a second opening on the distal end 364 of second portion 360.

Handle 308 has a first configuration and a second configuration and is moved between the first and second configuration by attaching second portion 346 to first portion 344 (e.g., screwing threaded portion 374 onto threaded portion 354) and removing second portion 346 from first portion 344 (e.g., unscrewing threaded portion 374 from threaded portion 354). In the first configuration, illustrated in FIG. 4A, projections 356 are free of recess 368 and define a first inside diameter. In the second configuration, illustrated in FIG. 4, projections 356 are disposed within recess 368 and define a second inside diameter. The second inside diameter is less than the first inside diameter and is sized and configured to provide contact between projections 356 and second light fiber 310 such that second light fiber 310 is attached to handle 308. The portion of second light fiber 310 attached to handle 308 is fixed (e.g., releasably attached) relative to handle 310 when handle 308 is in the second configuration and is moveable relative to handle 308 when handle is in the first configuration.

Housing 302 and handle 308 can be formed of any suitable material and using any suitable method of manufacture. Example materials considered suitable include, but are not limited to, metals, plastics, biocompatible materials, materials that can be made biocompatible, those described herein, and any other material considered suitable for a particular application. In addition, while the first portion 344 of handle 308 has been described as having threaded portion 354 and the second portion 346 of handle 308 has been described as having threaded portion 374, other methods of providing releasable attachment between the two components are considered suitable, and skilled artisans will be able to select a suitable type of attachment based on various considerations, such as the materials forming a first light fiber and/or second light fiber. Example methods of attachment considered suitable between the first portion and the second portion of a handle include, but are not limited to, providing a snap fit, morse taper, pin-vise, and any other method of attachment considered suitable for a particular embodiment.

The distal end 336 of first light fiber 306 is disposed within passageway 358 and attached to first portion 344 of handle 308 (e.g., at proximal end 334). Any suitable method of attachment is considered suitable, such as using adhesives, mechanical connections, welds, those described herein, and any other method of attachment considered suitable for a particular embodiment. Alternatively, first light fiber 306 can be positioned such that the distal end 336 is disposed at the proximal end 348 or distal end 350 of first portion 344.

Second light fiber 310 has a proximal end 378, a distal end 380, a length 381 extending from the proximal end 378 to the distal end 380, and defines a light path 382 extending along its length 381. In the illustrated embodiment, second light fiber 310 has a length 381 equal to 3.0 inches and an outside diameter equal to 0.5 millimeters. In the illustrated embodiment, second light fiber 310 omits the inclusion of a coating. However, alternative embodiments could include a coating on the second light fiber of a delivery system, such as the coatings described above with respect to first light fiber 306.

Each of the first light fiber 306 and second light fiber 310 can comprise any suitable light fiber. For example, commercially available optical fibers are considered suitable for use in the delivery system described herein and include, but are not limited to, plastic optical fibers and glass optical fibers, with or without cladding. While particular diameters and/or lengths have been described above with respect to the first light fiber 306 and second light fiber 310, the first light fiber and second light fiber of a delivery system can have any suitable diameter and/or length. Skilled artisans will be able to select a suitable diameters and/or length for a light fiber according to a particular embodiment based on various considerations, including the configuration of the housing and/or handle of a system. Example outside diameters considered suitable for a light fiber include, but are not limited to, a diameter between 0.3 millimeters and 0.7 millimeters, a diameter between about 0.3 millimeters and about 0.7 millimeters, a diameter equal to about 0.5 millimeters, a diameter equal to 0.5 millimeters, and any other outside diameter considered suitable for a particular embodiment. Example lengths considered suitable for a light fiber include, but are not limited to, a length between 2.0 inches and 5.0 inches, a length between about 2.0 inches and about 5.0 inches, a length equal to about 3.0 inches, a length equal to 3.0 inches, a length equal to 2.0 feet, a length equal to about 2.0 feet, a length between about 1.0 foot and about 3.0 feet, a length between 1.0 foot and 3.0 feet, and any other length considered suitable for a particular embodiment.

In use, the proximal end 378 of second light fiber 310 is passed through the passageway 370 defined by the second portion 346 of handle 308 and into the distal portion 360 of passageway 358 defined by the first portion 344 of handle 308. Subsequently, the second portion 346 of handle 308 is attached to the first portion 344 of handle 308 such that the handle 308 moves from its first configuration to its second configuration and second light fiber 310 is attached to handle 308. Second light fiber 310 is disposed within handle 308 such that its proximal end 378 is in communication with the distal end 336 of first light fiber 306. Light path 382 of second light fiber 310 is in communication with light path 338 of first light fiber 306 allowing light generated by light source 304 to travel through each of light path 338 and light path 382. Light can be emitted from second light fiber 310 radially and axially from its distal end 380. Alternatively, if a second light fiber included a coating, light can be directed axially from its distal end only.

Figure 5A:
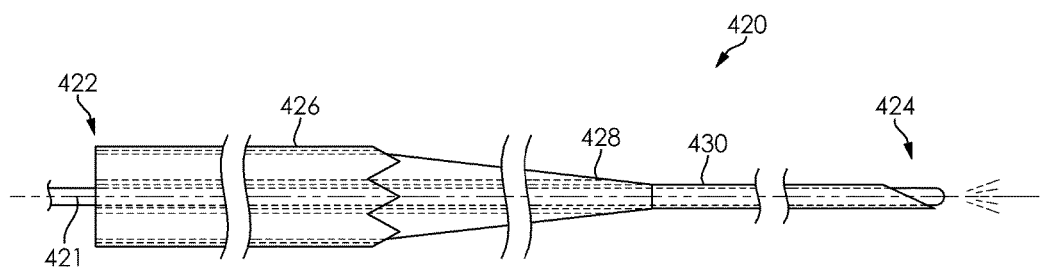
FIG. 5A illustrates a side view of an embodiment of an access system disposed over a light fiber.
Figure 5B:
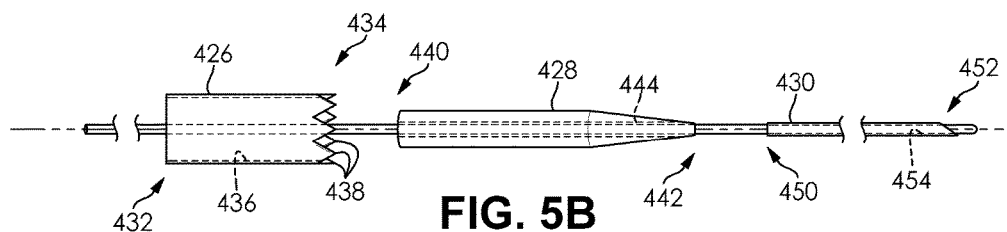
FIG. 5B illustrates is an exploded view of the access system illustrated in FIG. 5A.

FIG. 5 is an embodiment of a kit 400 that has a first medical device 402 according to an embodiment, such as medical device 10 illustrated in FIG. 1; a second medical device 404 according to an embodiment, such as medical device 110 illustrated in FIG. 2; a third medical device 406 according to an embodiment, such as medical device 210 illustrated in FIG. 3; a delivery system 408 according to an embodiment, such as delivery system 300 illustrated in FIG. 4; a first delivery tool 410; a second delivery tool 412; a third delivery tool 414; instructions for use 416, and an access system 418 according to an embodiment, such as access system 420 illustrated in FIG. 5A.

The first delivery tool 410 has a distal end with first configuration (e.g., Phillips head), the second delivery tool 412 has a distal end with a second configuration (e.g., flat head), and the third delivery tool has a distal end with a third configuration (e.g., hexagonal head). The first configuration is different than the second and third configuration and the second configuration is different than the first and third configuration. The first delivery tool 410, second delivery tool 412, and third delivery tool 414 have a distal end that is sized and configured to engage with a medical device to rotatably advance or rotatably withdraw the medical device into, or out of, a passageway defined by the wall of a body (e.g., thyroid cartilage). Example configurations considered suitable for the distal end of a delivery tool include, but are not limited to, hexagonal, triangular, square, pentagonal, slotted, cross-recesses, Phillips, Frearson, French recess, Mortorq, Pozidriv, Supadriv, Robertson, hex socket, hexalobular, TTAP, Phillips-square, Bristol, spline, spanner, Torq-set, TP3, tri-wing, triple square, or any other configuration considered suitable for a particular application. Alternative to, or in combination with, the delivery tools illustrated in kit 400, one or more delivery tools that define a passageway that extends from a first opening defined on the proximal end of the delivery tool to a second opening defined on the distal end of the delivery tool can be include in a kit.

While kit 400 has been described as including a first medical device 402, second medical device 404, a third medical device 406, first delivery tool 410, second delivery tool 412, third delivery tool 414, and an access system 418, a kit can include any suitable number of medical devices, delivery tools, and/or access systems. Skilled artisans will be able to select a suitable number of medical devices, delivery tools, and/or access systems to include in a kit according to a particular embodiment based on various considerations, including the type of treatment intended to be performed using the medical device and delivery tool. Example number of medical devices, delivery tools, and/or access systems considered suitable to include in a kit include, but are not limited to, one, at least one, two, a plurality, three, four, five, and any other number considered suitable for a particular application.

FIG. 5A illustrates an embodiment of an access system 420 disposed over a light fiber and adapted to create a passageway within the wall of a portion of the body (e.g., thyroid cartilage). Access system 420 has a longitudinal axis 421, a proximal end 422, a distal end 424, a sheath 426, dilator 428, and a needle 430. Needle 430 is slidably disposed within dilator 428 and dilator 428 is slidable disposed within sheath 426. In use, access system 420 is passed over a wire guide (e.g., second light fiber 310) and advanced into a passageway defined by the wall of a portion of the body (e.g., thyroid cartilage) and can be used to widen the passageway and/or introduce a medical device, as described in more detail herein.

Sheath 426 has a proximal end 432, a distal end 434, and defines a passageway 436 that extends from an opening on the proximal end 432 to an opening on the distal end 434. Passageway 436 is sized and configured to receive dilator 428 and allow dilator 428 to be passed through sheath 426. The distal end 434 of sheath 426 defines a plurality of teeth 438 that extend about the entirety of the circumference of distal end 434. Optionally, a sheath can include one or more elongate members that extend on an axis orthogonal to the lengthwise axis of the sheath that can be used to advance and/or rotate the sheath during use (e.g., to create, or widen, a passageway).

While sheath 426 has been illustrated as including a plurality of teeth 438, a sheath can include any suitable number of teeth, or omit the inclusion of teeth. Skilled artisans will be able to select a suitable number of teeth to include on a sheath according to a particular embodiment based on various considerations, including the material that the sheath is intended to contact. Example number of teeth considered suitable to include on a sheath include zero (e.g., distal end is similar to proximal end), one, at least one, two, a plurality, three, four, five, and any other number considered suitable for a particular embodiment.

Dilator 428 has a proximal end 440, a distal end 442, and defines a passageway 444 that extends from an opening on the proximal end 440 to an opening on the distal end 442. Passageway 444 is sized and configured to receive needle 430 and allow needle 430 to be passed through dilator 428.

Needle 430 has a proximal end 450, a distal end 452, and defines a passageway 454 that extends from an opening on the proximal end 450 to an opening on the distal end 452. Passageway 454 is sized and configured to receive a wire guide (e.g., second light fiber 310) and allow the wire guide to be passed through needle 430. The distal end 452 of needle 430 is tapered. Alternatively, the distal end of a needle can be flat, or substantially flat.

Any of the elements, features, and/or structural arrangements described herein with respect to any medical device, delivery system, delivery tool, and/or access system can be combined in any suitable manner. Skilled artisans will be able to select a suitable element, feature, and/or structural arrangement to include in a medical device, delivery system, delivery tool, and/or access system according to a particular embodiment based on various considerations, such as the structural arrangement at a point of treatment within which a medical device, delivery system, delivery tool, and/or access system is intended to be used.

Methods of treatment are described herein. While the methods described herein are shown and described as a series of acts, it is to be understood and appreciated that the methods are not limited by the order of acts, as some acts may in accordance with these methods, be omitted, be repeated, or occur in different orders and/or concurrently with other acts described herein.

Figure 6:
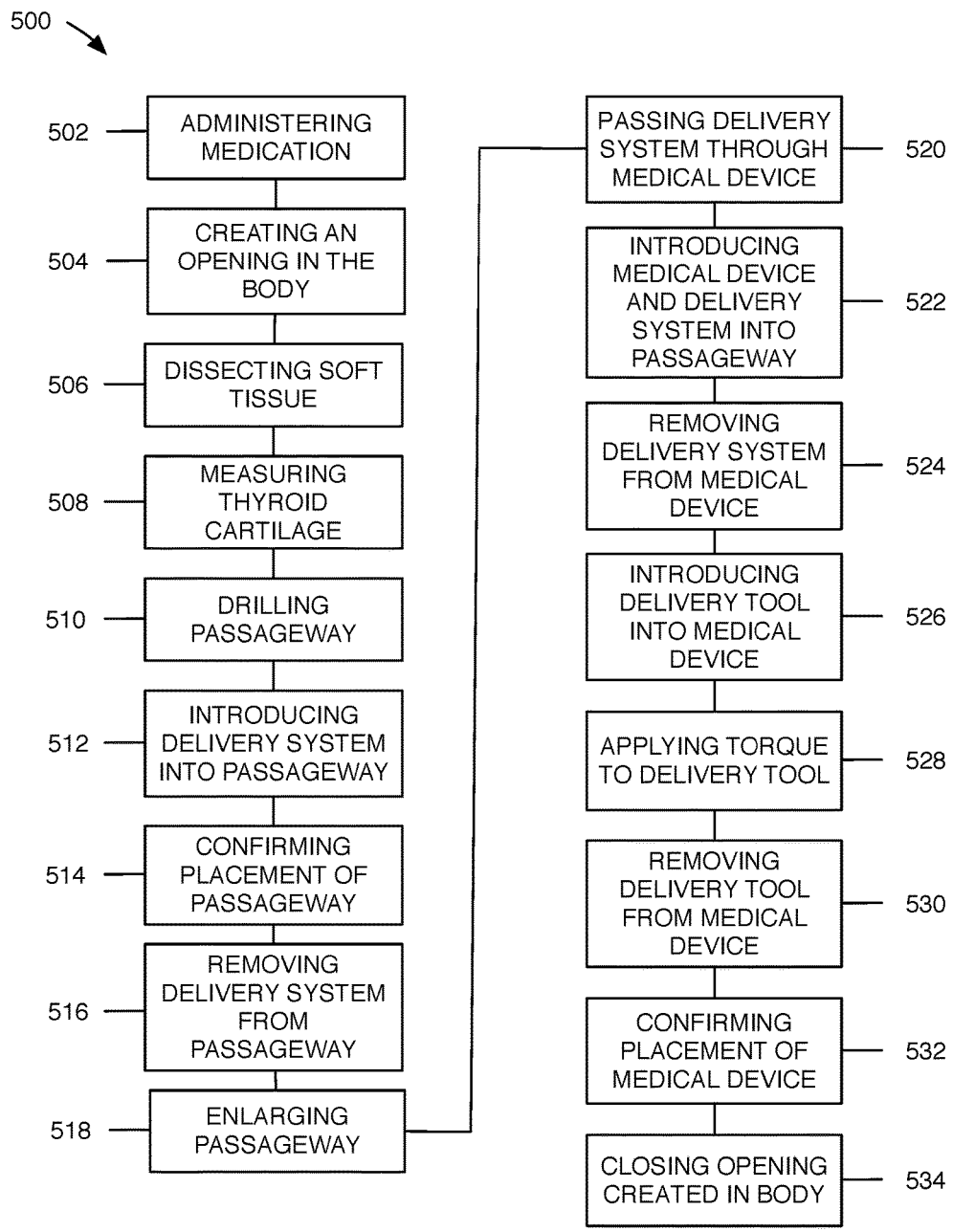
FIG. 6 is a flowchart representation of a method of treatment.

FIG. 6 is a flowchart representation of an exemplary method 500 of medializing a vocal cord within the larynx.

A step 502 comprises administering a medication near a point of treatment. Another step 504 comprises creating an opening in the body over the thyroid cartilage. Another step 506 comprises dissecting the underlying soft tissues to expose the thyroid cartilage. Another step 508 comprises measuring the thyroid cartilage. Another step 510 comprises drilling a passageway in the thyroid cartilage. Another step 512 comprises introducing the distal end of a delivery system into the passageway. Another step 514 comprises confirming placement of the passageway. Another step 516 comprises removing the delivery system from the passageway. Another step 518 comprises enlarging the passageway. Another step 520 comprises passing the distal end of the delivery system through a medical device. Another step 522 comprises introducing the distal end of the medical device and the distal end of the delivery system into the passageway. Another step 524 comprises removing the delivery system from the medical device. Another step 526 comprises introducing the distal end of a delivery tool into the medical device. Another step 528 comprises applying torque to the delivery tool such that the medical device is rotatably advanced into passageway. Another step 530 comprises removing the delivery tool from the medical device. Another step 532 comprises confirming placement of the medical device. Another step 534 comprises closing the opening created in the body.

Step 502 can be accomplished by administering any suitable medication at any suitable location on the body of a patient. For example, medication can be administered on the side of the vocal cord being treated (e.g., paralyzed vocal cord) and over the thyroid cartilage. Any suitable medication such as a local anesthetic, combination of local anesthetic and vasoconstrictor (e.g., 1% lidocaine, with 1:100,000 epinephrine), and/or general anesthetic can be used and administered in any suitable manner, such as subcutaneously using a convention syringe.

An optional step that can be completed prior to step 502 comprises prepping the patient. This optional step can be accomplished by draping the patient. Another optional step that can be completed prior to step 502 comprises positioning the patient in the supine position on an operating table. This step can optionally be accomplished utilizing a shoulder roll. Another optional step comprises administering a sedative to the patient.

Step 504 can be accomplished using any suitable medical device (e.g., scalpel) and by creating the opening on the side of the vocal cord that is being treated and over the thyroid cartilage. Step 504 can be accomplished by creating an opening that is sized and configured to allow a delivery system and/or medical device to pass through the opening. Example lengths of an opening considered suitable include, but are not limited to, lengths that are between 4.0 centimeters and 6.0 centimeters, between about 4.0 centimeters and about 6.0 centimeters, and any other length considered suitable for a particular method of treatment.

Step 506 can be accomplished using any suitable medical device such that the thyroid cartilage (e.g., lateral aspect of thyroid cartilage) is exposed and the perichondrium is left intact. For example, step 506 can be accomplished using one or more of a needle, probe, pick, scalpel, forceps, tweezers, scissors, or any other device considered suitable for a particular procedure. Optionally, step 506 can be omitted from method 500.

Step 508 can be accomplished using any suitable measuring device (e.g., ruler) and by measuring the thyroid cartilage from the notch at its superior aspect to the inferior margin. The midpoint between these two features represents the level of the vocal fold. An optional step comprises marking the thyroid cartilage at the midpoint between the notch at its superior aspect and the inferior margin.

An optional step comprises measuring the thyroid cartilage between the anterior and inferior aspects of the thyroid cartilage. This optional step can be accomplished using any suitable measuring device (e.g., ruler). An optional step comprises marking the thyroid cartilage at the midpoint between the anterior and inferior aspects of the thyroid cartilage.

Step 510 can be accomplished by locating the midpoint (e.g., marking) between the notch at the superior aspect of the thyroid cartilage and the inferior margin of the thyroid cartilage and drilling a passageway between the anterior and posterior aspects of the thyroid cartilage. Step 510 can be accomplished using any suitable drill and a drill bit that has a first outside diameter. The diameter of the passageway created is sized and configured to allow the distal end and a portion of a delivery system, light fiber, medical device, or other visualization device, to pass through the passageway. The depth of the passageway traverses the thyroid cartilage such that the distal end of the medical device, delivery system, light fiber, or other visualization device passed through the passageway can be disposed between the thyroid cartilage and the vocal cord being treated. An optional step that can be completed in combination with, or separate from, step 510 comprises locating the midpoint (e.g., marking) between the anterior and inferior aspects of the thyroid cartilage.

A drill bit used complete any step of the methods described herein can have any suitable outside diameter, and skilled artisans will be able to select a suitable outside diameter for a drill bit according to a particular embodiment based on various considerations, including the structural arrangement at a point of treatment. Example outside diameters considered suitable for a drill bit include outside diameters between 0.75 millimeters to 2.0 millimeters, outside diameters between about 0.75 millimeters and about 2.0 millimeters, and any other outside diameter considered suitable for a particular embodiment.

Step 512 can be accomplished by applying a distally-directed force on any suitable portion (e.g., housing 302 and/or handle 308) of any suitable delivery system according to an embodiment, such as the embodiments described and illustrated herein. The distal end of the delivery system can be disposed within the passageway, or distal to the distal end of the passageway. Skilled artisans will be able to select a suitable delivery system to introduce into a passageway according to an embodiment based on various considerations, including the diameter and depth of the passageway created in the thyroid cartilage. Example delivery systems considered suitable include, but are not limited to, delivery system 300, and any other delivery system considered suitable for a particular application. Alternatively, the distal end of a light fiber, or other visualization device, independent of a delivery system can be passed through a portion, or the entirety, of the passageway created in the thyroid cartilage by applying a distally-directed force on any suitable portion of the device. An optional step comprises activating the light source of the delivery system, light fiber, or other visualization device.

Step 514 can be accomplished using any suitable method of visualizing light being generated by the delivery system and being emitted from a light fiber (e.g., second light fiber 310). Alternatively, if a light fiber or other visualization device has been passed through the passageway, this step can be accomplished using any suitable method of visualizing the light being emitted from the light fiber or other visualization device. For example, an optional step comprises introducing a scope (e.g., flexible fiber optic scope) into an airway of a patient (e.g., mouth, nasal opening) such that the distal end of the scope is disposed above the thyroid cartilage. Another optional step comprises viewing the light emitted from the delivery system, light fiber, or other visualization device disposed through the passageway. Alternatively, the position of the light emitted from the delivery system, light fiber, or other visualization device, can be confirmed transcutaneously.

If the passageway created in the thyroid cartilage is not positioned such that placement of a medical device will provide proper treatment (e.g., medialize the vocal cord), an optional step comprises drilling a second passageway relative to the passageway created in step 510. This can be accomplished by completing an optional step that comprises measuring the thyroid cartilage from the first passageway to a second location relative to the first passageway and repeating step 510 at the second location. Subsequent to creating the second passageway, step 512 and step 514 can be completed relative to the second passageway to determine if the second passageway is in a position that will provide proper treatment (e.g., medialize the vocal cord being treated) and step 516, step 518, step 520, step 522, step 524, step 526, step 528, step 530, step 532, step 534, and/or any of the alternative and/or optional steps described herein, can be completed to implant a medical device according to an embodiment, such as those described herein, within the second passageway.

Step 516 can be accomplished by applying a proximally-directed force on any suitable portion of the delivery system until the distal end of the delivery system has been removed from the passageway created in the thyroid cartilage. Alternatively, if a light fiber or other visualization device has been passed through the passageway created in the thyroid cartilage, an optional step comprises apply a proximally-directed force on any suitable portion of the light fiber or other visualization device until the distal end has been removed from the passageway.

Step 518 can be accomplished using any suitable drill and a drill bit that has a second outside diameter that is greater than the first outside diameter of the drill bit used to complete step 510. The diameter of the passageway created in the thyroid cartilage is sized and configured to allow a medical device according to an embodiment to be implanted within the enlarged passageway created by the second drill bit. The depth of the passageway created by the second drill bit traverses the thyroid cartilage.

Step 520 can be accomplished by passing the distal end of the delivery system through a portion, or the entirety, of the length of any suitable medical device according to an embodiment, such as the embodiments described and illustrated herein. Skilled artisans will be able to select a suitable medical device to pass a portion of a delivery system through and to introduce into a passageway created in the thyroid cartilage according to a particular embodiment based on various considerations, including the structural configuration of the thyroid cartilage. Example medical devices considered suitable include, but are not limited to, medical device 10, medical device 110, medical device 210, and any other medical device considered suitable for a particular application.

For example, step 520 can be accomplished using medical device 110 and delivery system 300. The distal end 380 of second light fiber 310 is passed through proximal passageway 126, main passageway 160, and distal passageway 158 such that it is disposed distal to the distal end 114 of medical device 110.

Step 522 is accomplished by applying a distally-directed force on each of the delivery system and medical device such that the distal end of the delivery system and the distal end of the medical device are advanced into the passageway created in the thyroid cartilage. Optionally, step 522 can be completed in two separate steps. A first step comprises advancing the distal end of the delivery system into the passageway created in the thyroid cartilage by applying a distally-directed force on the delivery system. This allows the delivery system to be used as a wire guide for advancement of the medical device into the passageway. A second step comprises advancing the distal end of the medical device into the passageway crated in the thyroid cartilage by applying a distally-directed force on the medical device. Optionally, the light source of the delivery system can be activated and emit light prior to, subsequent to, or in combination with, this step, or any other step described herein.

Step 524 can be accomplished by applying a proximally-directed force on any suitable portion of the delivery system until the distal end of the delivery system is removed from the medical device and the passageway created in the thyroid cartilage.

Alternatively, step 520, step 522, and step 524 can be omitted and an alternative step that comprises introducing the medical device into the passageway can be completed. This step can be accomplished, for example, using a medical device such as medical device 10 illustrated in FIG. 1 that does not define a passageway that extends along its length.

If a delivery tool that defines a passageway from its proximal end to its distal end is being used to implant the medical device, an alternative step comprises moving the handle of the delivery system (e.g., handle 308) from its second configuration to its first configuration such that the second light fiber (e.g., second light fiber 310) can be removed from the delivery system and its position maintained within the medical device and the passageway created in the thyroid cartilage.

Alternatively, step 520, step 522, and step 524 can be omitted and an alternative step that comprises introducing the delivery system into the passageway created in the thyroid cartilage can be completed. This step can be accomplished as described above with respect to step 512. Optionally, step 516 and step 518 can be omitted from method 500 and this alternative step can replace step 512 such that the passageway created in step 510 is used to implant a medical device. Another alternative step comprises moving the delivery system (e.g., handle 308) from its second configuration to its first configuration such that the second light fiber (e.g., second light fiber 310) can be removed from the delivery system and its position maintained with the passageway created within the thyroid cartilage. Another alternative step comprises advancing a medical device over the second light fiber and through the passageway defined by the medical device. This step can be accomplished by passing the proximal end (e.g., proximal end 378) of the second light fiber (e.g., second light fiber 310) through the distal passageway (e.g., distal passageway 158), main passageway (e.g., main passageway 160), and proximal passageway (e.g., 126) of the medical device such that the second light fiber acts as a wire guide for the introduction of the medical device into the passageway.

If a delivery tool that defines a passageway from its proximal end to its distal end is being used to implant the medical device, an alternative step comprises passing the proximal end of the second light fiber (e.g., proximal end 378) through the distal opening of the delivery tool and through the passageway of the delivery tool such that the second light fiber acts a wire guide for the delivery tool. Another alternative step comprises applying a distally-directed force on any suitable portion of the delivery tool until the distal end of the delivery tool is disposed within a passageway defined by the medical device. Another alternative step comprises removing the second light fiber from the medical device.

Step 526 can be accomplished by apply a distally-directed force on any suitable delivery tool according to an embodiment, such as the embodiments described and illustrated herein, until the distal end of the delivery tool is disposed within a passageway defined by the medical device. Skilled artisans will be able to select a suitable delivery tool to introduce into a medical device according to a particular embodiment based on various considerations, including the structural configuration of the passageway defined by the medical device. Example delivery tools considered suitable include, but are not limited to, those described herein, delivery tool 410, delivery tool 412, delivery tool 414, delivery tools that define a passageway that extends from the proximal end to the distal end of the delivery tool, and any other delivery tool considered suitable for a particular application.

Figure 6A:
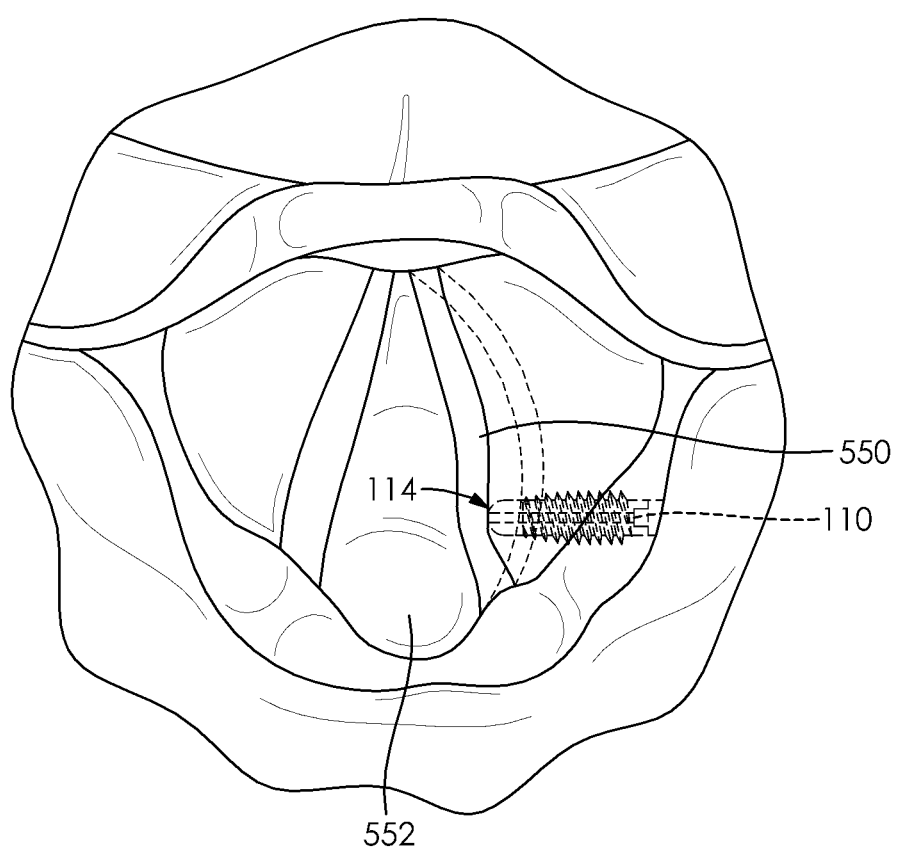
FIG. 6A is a sectional view of an airway of a patient, within which an embodiment of a medical device has been implanted.

Step 528 can be accomplished by applying torque to any suitable portion of the delivery tool such that the distal end of the delivery tool engages with the inner surface of a passageway defined by the medical device and transfers the applied torque to the medical device. Torque can be applied in the clockwise direction to rotatably advance the medical device into the passageway. An optional step comprises applying torque to any suitable portion of the delivery tool in the counterclockwise direction to rotatably withdraw the medical device from the passageway. The torque applied to the delivery tool is relative to the longitudinal axis of the medical device and can be applied until the medical device contacts and medializes the vocal cord being treated. Torque is applied to the delivery tool until a predetermined, or desired, final position the vocal cord being treated has been achieved. For example, torque is applied to delivery tool until the vocal cord being treated has been medialized and/or desired timbre has been achieved. FIG. 6A illustrates a vocal cord 550 being treated with medical device 110. The position of the vocal cord 550 being treated prior to implantation of medical device 110 is shown in hidden lines and the position of the vocal cord 550 being treated after implantation of medical device 110 is shown in solid lines. As shown in FIG. 6A, the distal end 114 of medical device 110 is contacting the vocal cord 550 such that it is medialized relative to the larynx 552.

An optional step comprises instructing the patient to phonate while step 528, or the optional step of applying torque to the delivery tool in the counterclockwise direction, is being completed such that the position of the distal end of the medical device relative to the vocal cord can be adjusted to achieve a desired timbre. Alternatively, this optional step can be completed subsequent to completion of step 528, or the optional step of applying torque to the delivery tool in the clockwise direction, such that the position of the medical device relative to the vocal cord can be adjusted to achieve a desired timbre. Another optional step comprises repeating step 528, or the optional step of applying torque in the counterclockwise direction, to adjust the placement of the distal end of the medical device relative to the vocal cord being treated. Another optional step comprises repeating the step of instructing the patient to phonate while repeating step 528, or the optional step of applying torque to the delivery tool in the counterclockwise direction.

Step 530 can be accomplished by applying a proximally-directed force on any suitable portion of the delivery tool until the delivery tool has been removed from the medical device.

Step 532 can be accomplished by instructing the patient to phonate. Proper placement of the medical device can be determined by instructing the patient to phonate in a normal voice, shouting voice, and/or singing voice to determine if the correct timbre has been achieved. If the correct timbre has not been achieved, one or more of the above steps, optional steps, and/or alternative steps can be repeated (e.g., step 526, step 528, step 530) until a desired timbre has been achieved. Optionally, if the correct timbre has not been achieved, one or more additional medical devices can be implanted relative to the first medical device at a location different from the location the first medical device. Each of the one or more additional medical devices can be adjusted alone, or relative to each other and/or the first medical device, to achieve a desired timbre. This can be accomplished by repeating step 502, step 504, step 506, step 508, step 510, step 512, step 514, step 516, step 518, step 520, step 522, step 524, step 526, step 528, step 530, step 532, any of the alternative steps described herein, any of the optional steps described herein, and/or any other step considered suitable for a particular method of treatment.

Step 534 can be accomplished using any suitable device and/or method, such as by suturing the opening created in step 504. Optionally, this step can be accomplished closing the opening in layers.

While method 500 has been described with respect to treating a vocal cord, any of the steps, alternative steps, and/or optional steps described herein can be utilized at any suitable point of treatment to provide any suitable treatment. Skilled artisans will be able to select a suitable point of treatment and to implant a medical device according to an embodiment based on various considerations, including the type treatment intended to be performed and the structural arrangement at the treatment site.

While various steps, alternative steps, and optional steps have been described above with respect to a method of treatment 500, these steps, alternative steps, and optional steps can be included in, accomplished concurrently with, and/or accomplished in the alternative to, the methods, steps, alternative steps, and/or optional steps described below with respect to method of treatment 600.

Figure 7:
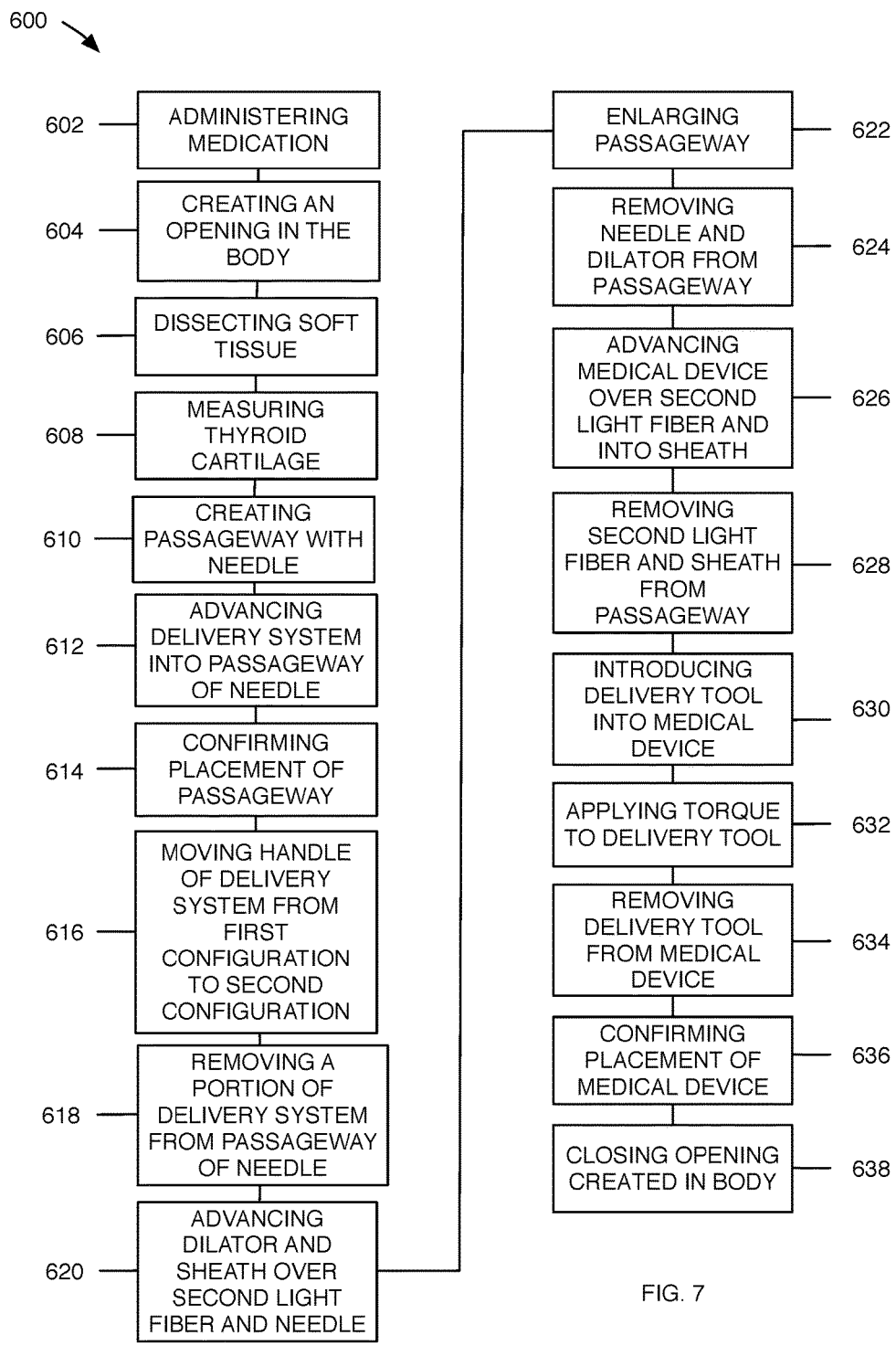
FIG. 7 is a flowchart representation of another method of treatment.

FIG. 7 is a flowchart representation of another exemplary method 600 of medializing a vocal cord within the larynx.

A step 602 comprises administering a medication near a point of treatment. Another step 604 comprises creating an opening in the body over the thyroid cartilage. Another step 606 comprises dissecting the underlying soft tissues to expose the thyroid cartilage. Another step 608 comprises measuring the thyroid cartilage. Another step 610 comprises creating a passageway in the thyroid cartilage with a needle. Another step 612 comprises advancing the distal end of a delivery system into the passageway defined by the needle. Another step 614 comprises confirming placement of the passageway created in the thyroid cartilage. Another step 616 comprises moving the handle of the delivery system from the first configuration to the second configuration. Another step 618 comprises removing a portion of the delivery system from the passageway of the needle while maintaining the position of the second light fiber within the passageway defined by the needle. Another step 620 comprises advancing the dilator and sheath over the second light fiber and needle. Another step 622 comprises enlarging the passageway. Another step 624 comprises removing the needle and dilator from the passageway created in the thyroid cartilage and the passageway defined by the sheath. Another step 626 comprises advancing a medical device over the second light fiber and into the passageway defined by the sheath. Another step 628 comprises removing the second light fiber and sheath from the passageway created in the thyroid cartilage. Another step 630 comprises introducing the distal end of a delivery tool into the medical device. Another step 632 comprises applying torque to the delivery tool such that the medical device is rotatably advanced into passageway. Another step 634 comprises removing the delivery tool from the medical device. Another step 636 comprises confirming placement of the medical device. Another step 638 comprises closing the opening created in the body.

Step 602 can be accomplished as described above with respect to step 502. Step 604 can be accomplished as described above with respect to step 504. Step 606 can be accomplished as described above with respect to step 506. Step 608 can be accomplished as described above with respect to step 508.

Step 610 can be accomplished by locating the midpoint (e.g., marking) between the notch at the superior aspect of the thyroid cartilage and the inferior margin of the thyroid cartilage and applying a distally-directed force on any suitable portion of a needle to create a passageway between the anterior and posterior aspects of the thyroid cartilage. Step 610 can be accomplished using any suitable needle that has any suitable outside diameter. The diameter of the passageway created is sized and configured to allow the distal end and a portion of a delivery system, light fiber, medical device, or other visualization device, to pass through the passageway. The depth of the passageway traverses the thyroid cartilage such that the distal end of the medical device, delivery system, light fiber, or other visualization device passed through the passageway can be disposed between the thyroid cartilage and the vocal cord being treated. An optional step that can be completed in combination with, or separate from, step 610 comprises locating the midpoint (e.g., marking) between the anterior and inferior aspects of the thyroid cartilage Step 610 can be accomplished using any suitable needle according to an embodiment, such as the embodiments described and illustrated herein (e.g., needle 430). Skilled artisans will be able to select a suitable needle to create a passageway within the thyroid cartilage according to an embodiment based on various considerations, including the diameter and depth of the passageway intended to be created in the thyroid cartilage. Example needles considered suitable include, but are not limited to, needle 430, and any other needle considered suitable for a particular application.

Step 612 can be accomplished by applying a distally-directed force on any suitable portion (e.g., housing 302 and/or handle 308) of any suitable delivery system according to an embodiment, such as the embodiments described and illustrated herein. The distal end of the delivery system can be disposed within the passageway defined by the needle, or distal to the distal end of the passageway defined by the needle. Skilled artisans will be able to select a suitable delivery system to introduce into a passageway defined by a needle according to an embodiment based on various considerations, including the diameter and length of the needle being used. Example delivery systems considered suitable include, but are not limited to, delivery system 300, and any other delivery system considered suitable for a particular application.

Step 614 can be accomplished as described above with respect to step 514.

Step 616 can be accomplished by applying torque to the handle in the counterclockwise direction to remove the second portion of the handle from the first portion of the handle.

Step 618 can be accomplished by applying a proximally-directed force on any suitable portion of the delivery system (e.g., first portion of handle, second portion of handle) while the position of the second light fiber is maintained within the passageway defined by the needle. For example, this step can be accomplished by applying a proximally-directed force on any suitable portion of the delivery system until the second portion of the handle has been removed from the second light fiber.

Step 620 can be accomplished by applying a distally-directed force on any suitable portion of a dilator and sheath such that the dilator and sheath are advanced over the needle and second light fiber. Step 620 can be accomplished using any suitable dilator and sheath according to an embodiment, such as the embodiments described and illustrated herein (e.g., sheath 426, dilator 428). Skilled artisans will be able to select a suitable dilator and sheath to advance over a needle and second light fiber according to an embodiment based on various considerations, including the diameter and depth of the passageway intended to be created in the thyroid cartilage. Example sheaths considered suitable include, but are not limited to, sheath 426, and any other sheath considered suitable for a particular application. Example dilators considered suitable include, but are not limited to, dilator 428, and any other dilator considered suitable for a particular application.

Step 622 can be accomplished by rotating, or advancing, the dilator and sheath over the needle and into the passageway created in the thyroid cartilage. Alternatively, this step can be accomplished in two separate steps. A first step that comprises advancing the dilator over the needle and into the passageway created in the thyroid cartilage and a second step that comprises advancing the sheath over the dilator and into the passageway created in the thyroid cartilage. The first step can accomplish enlarging the passageway created in the thyroid cartilage using the tapered configuration of the dilator and by applying a distally-directed force on any suitable portion of the dilator. The second step can accomplish enlarging the passageway created in the thyroid cartilage by applying a distally-directed force, or torque, to any suitable portion of the sheath.

Step 624 can be accomplished by applying a proximally-directed force on any suitable portion of the needle and dilator until the needle and dilator have been removed from the passageway created in the thyroid cartilage and the passageway defined by the sheath. Alternatively, this step can be completed in two separate steps. A first step that comprises applying a proximally-directed force on any suitable portion of the needle and a second step that comprises applying a proximally-directed force on any suitable portion of the dilator.

Step 626 can be accomplished by passing the proximal end of the second light fiber through the passageway defined by a medical device and applying a distally-directed force on any suitable portion of the medical device until the distal end of the medical device is disposed within the passageway defined by the sheath and/or the proximal end of the passageway created in the thyroid cartilage. Any suitable medical device according to an embodiment can be used to accomplished step 626, such as the embodiments described and illustrated herein. Skilled artisans will be able to select a suitable medical device to pass a second light fiber through and to introduce into a passageway created in a sheath and/or the thyroid cartilage according to a particular embodiment based on various considerations, including the structural configuration of the thyroid cartilage. Example medical devices considered suitable include, but are not limited to, medical device 10, medical device 110, medical device 210, and any other medical device considered suitable for a particular application.

An optional step comprises applying torque to the medical device being implanted to advance the medical device into the passageway created in the thyroid cartilage. This step can be accomplished using any suitable device, or one or more fingers.

An optional step that can be completed subsequent to step 626 comprises moving the handle of the delivery system from the second configuration to the first configuration to confirm placement of medical device. This can be accomplished by applying torque to the handle in the clockwise direction to releasably attach the second portion of the handle to the first portion of the handle and by activating the light source of the delivery system if not already activated.

Step 628 can be accomplished by applying a proximally-directed force on any suitable portion of the second light fiber and the sheath until the second light fiber and sheath have been removed from the passageway created in the thyroid cartilage. Alternatively, this step can be completed in two separate steps. A first step that comprises applying a proximally-directed force on any suitable portion of the second light fiber and a second step that comprises applying a proximally-directed force on any suitable portion of the sheath.

Step 630 can be accomplished as described above with respect to step 526. Step 632 can be accomplished as described above with respect to step 528. Step 634 can be accomplished as described above with respect to step 530. Step 636 can be accomplished as described above with respect to step 532. Step 638 can be accomplished as described above with respect to step 534.

While various steps, alternative steps, and optional steps have been described above with respect to a method of treatment 600, these steps, alternative steps, and optional steps can be included in, accomplished concurrently with, and/or accomplished in the alternative to, the methods, steps, alternative steps, and/or optional steps described above with respect to method of treatment 500.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A method of medializing a vocal cord within the larynx of a patient, comprising:
    making an incision over the thyroid cartilage of said patient;
    dissecting soft tissue underlying the incision to expose the lateral aspect of the thyroid cartilage of said patient;
    drilling a hole in the thyroid cartilage of said patient at a point half way between the anterior and posterior aspects of the thyroid cartilage;
    placing a light source through the hole;
    viewing light emitted from the light source; and
    advancing a medical device through the hole to move said vocal cord toward a midline of said larynx to achieve an artificial placement of said vocal cord.

2. The method of claim 1, further comprising enlarging the hole in the thyroid cartilage before advancing a medical device through the hole.

3. The method of claim 2, wherein the enlarging is performed subsequent to the viewing.

4. The method of claim 1, further comprising continuing the advancing of a medical device to adjust the position of the medical device and the artificial placement of the vocal cord until a desired artificial placement is achieved.

5. The method of claim 1, further comprising receding the medical device to adjust the position of the medical device and the artificial placement of the vocal cord until a desired artificial placement is achieved.

6. The method of claim 1, further comprising drilling a second hole in the thyroid cartilage of said patient.

7. The method of claim 6, further comprising advancing a second medical device through the second hole to move a vocal cord of said patient toward a midline of said larynx to achieve an artificial placement of the vocal cord.

8. The method of claim 1, further comprising having the patient speak in a normal voice, shout, and sing following the advancing a medical device through the hole.

9. A method of medializing a vocal cord within the larynx of a patient, comprising:
    making an incision over the thyroid cartilage of said patient;
    dissecting soft tissue underlying the incision to expose the lateral aspect of the thyroid cartilage of said patient;
    drilling a passageway in the thyroid cartilage of said patient;
    introducing a delivery system into the passageway, the delivery system comprising a light source;
    confirming placement of the passageway by visualizing light generated by the light source; and
    advancing a medical device through the passageway to move said vocal cord toward a midline of said larynx to achieve an artificial placement of said vocal cord.

10. The method of claim 9, further comprising continuing the advancing of a medical device to adjust the position of the medical device and the artificial placement of the vocal cord until a desired artificial placement is achieved.

11. The method of claim 9, further comprising removing the delivery system from the passageway and passing the delivery system through a medical device adapted to move said vocal cord toward a midline of said larynx to achieve an artificial placement of said vocal cord before the advancing.

12. The method of claim 9, further comprising enlarging the passageway in the thyroid cartilage before advancing a medical device through the passageway.

13. The method of claim 12, wherein the enlarging is performed subsequent to the confirming.

14. The method of claim 9, further comprising introducing a delivery tool into the medical device.

15. The method of claim 14, wherein the delivery tool is configured to engage the medical device.

16. The method of claim 15, further comprising applying torque to the delivery tool to achieve the advancing.

17. The method of claim 9, further comprising receding the medical device to adjust the position of the medical device and the artificial placement of the vocal cord until a desired artificial placement is achieved.

18. The method of claim 9, further comprising having the patient speak in a normal voice, shout, and sing following the advancing a medical device through the passageway.

19. The method of claim 9, wherein the advancing a medical device through the passageway is performed while said patient is phonating.

20. A method of medializing a vocal cord within the larynx of a patient, comprising:
    creating a passageway in thyroid cartilage of said patient;
    advancing a light source through the passageway;
    activating the light source to emit light;
    confirming a desired placement of the passageway relative to said vocal cord by visualizing light emitted from the light source relative to said vocal cord; and
    advancing a medical device through the passageway to move said vocal cord toward a midline of said larynx of said patient.

* * * * *